United States Patent [19]

Roy et al.

[11] Patent Number: 5,402,505
[45] Date of Patent: Mar. 28, 1995

[54] SEMICONDUCTOR DEVICE LEAD INSPECTION SYSTEM

[75] Inventors: Rajiv Roy, Garland; Charles K. Harris, Dallas, both of Tex.

[73] Assignee: Texas Instruments Incorporated, Dallas, Tex.

[21] Appl. No.: 138,791

[22] Filed: Oct. 18, 1993

[51] Int. Cl.⁶ .................. G01N 21/88; G06K 9/20
[52] U.S. Cl. ........................... 382/8; 348/126; 348/137; 356/397
[58] Field of Search ............ 382/8, 61, 63; 348/87, 348/126, 136, 137, 86, 92, 94, 95, 131, 135, 138, 139, 140, 141; 356/396, 397, 401, 237

[56] References Cited

U.S. PATENT DOCUMENTS

| | | | |
|---|---|---|---|
| 4,393,401 | 7/1983 | Gorenflo | 356/397 |
| 5,157,734 | 10/1992 | Chen et al. | 348/95 |
| 5,162,866 | 11/1992 | Tomiya et al. | 356/237 |
| 5,189,707 | 2/1993 | Suzuki et al. | 382/8 |
| 5,249,239 | 9/1993 | Kida | 382/8 |
| 5,268,743 | 12/1993 | Kida | 356/237 |

*Primary Examiner*—Joseph Mancuso
*Assistant Examiner*—Larry J. Prikockis
*Attorney, Agent, or Firm*—Warren L. Franz; Wade James Brady, III; Richard L. Donaldson

[57] ABSTRACT

The invention is to a system and apparatus for determining the planarity of leads on a semiconductor device. An image system is used to locate the leads with reference to a reference plate on which the device is mounted, and a real-time reference which is used to provide a known correlation between image pixels and linear measurement such as mils.

11 Claims, 4 Drawing Sheets

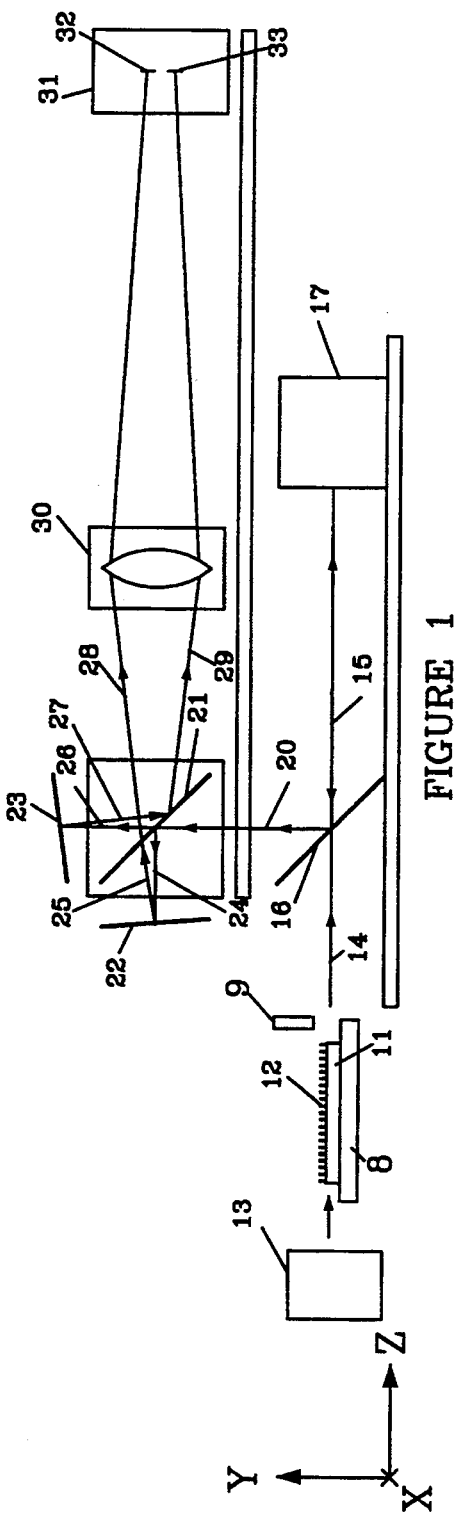
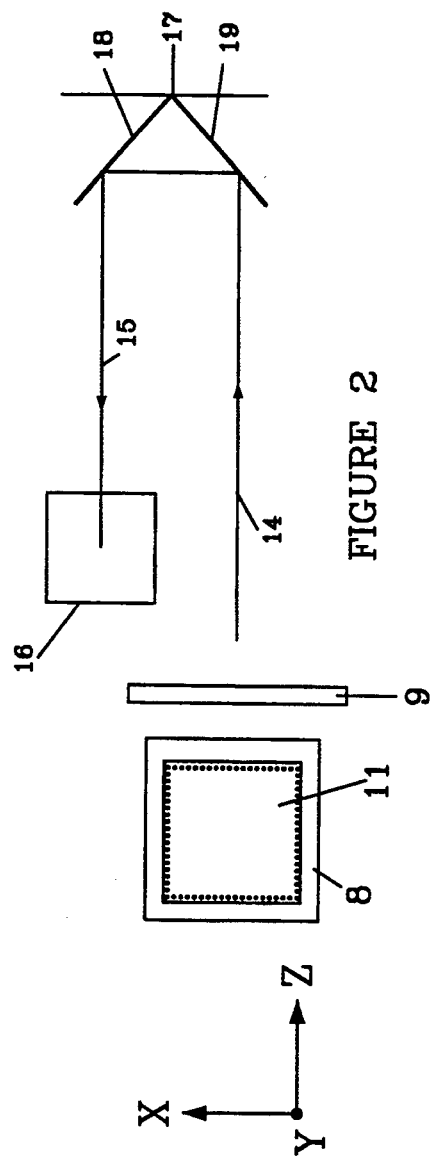
FIGURE 1
FIGURE 2

SEMICONDUCTOR DEVICE LEAD INSPECTION SYSTEM

FIELD OF THE INVENTION

This invention relates to semiconductor devices, and more particularly to an improved machine vision image system used to provide a referencing system for inspecting for coplanarity of leads on surface mount devices.

CROSS-REFERENCE

Application Ser. No. 08/043,333, filed Apr. 6, 1993, entitled SEMICONDUCTOR DEVICE LEAD INSPECTION SYSTEM.

BACKGROUND OF THE INVENTION

In testing and mounting semiconductor devices, it is necessary that the leads of the device be correctly positioned and that the ends of the leads lie in a common plane. This is particularly true for surface-mount devices. The leads of the semiconductor device may be bent sideways, out, in or down, thereby moving the end of the pin from a plane common with the ends of the other pins. In some instances, one or more pins may have a greater height than the others.

Existing planarity inspection equipment is either not cost-effective or performs the inspection "off-line" as in a quality control operation. The hardware required for off-line inspection is inexpensive; however, the inspection is done manually, lead by lead, making 100% inspection time-consuming, as well as labor cost prohibitive. Automatic equipment which can be used for on-line inspection is actually stand-alone equipment integrated with the other processing equipment.

In order to inspect for coplanarity of the leads of a surface-mount device using machine vision, the leads must be located, and the machine vision image converted to scale units such a millimeters or mils using a scale factor. The data has to be converted from multiple two-dimension coordinate frames to a three-dimensional coordinate frame using a plane for reference. Present systems using the above method for determining planarity have to be calibrated prior to each series of devices to be tested, and pixel jitter or motion, after calibration, is not detected during cap of the picture and may cause errors.

SUMMARY OF THE INVENTION

The invention provides a real-time reference system and method that (1) locates the leads on the device; and (2) converts captured image from pixels to dimensional units such a millimeters or mils, using a scale factor. The data is (3) transformed from multiple two-dimensional coordinates to a three-dimensional coordinate frame using a reference plate; and (4) the lead tips or ends are transformed to a reference plane to measure coplanarity. This plane may be computed either as a three-point seating plane, least squares linear regression through all the leads, or other technique of computing coplanarity.

The real-time reference of the invention provides information to help in steps (1), (2) and (3) above, by allowing the system to make the assumption that the leads will be somewhere just below the bottom edge of the real-time reference. If there is jitter, both the real-time reference and the device will move in the captured image. This provides compensation since if all computations are made with respect to the real-time reference, pixel jitter is irrelevant.

The real-time reference helps in step (2) since it provides square features of known dimensions from which pixels can be transformed into real-world dimensions.

In step (3), there are two alternatives:

(a) The bottom edge of the real-time reference is a flat plane. By making the real-time reference parallel to both the camera optical path and the platform plane on which the device is mounted, then it can be assumed that the bottom edge is a plane.

(b) The top surface on which the device is mounted is a plane. If the top surface on which the device is mounted is a plane, then a custom mounting surface for each type of device is not needed.

The system operates as follows:

The system scans and locates the top surface of the device mounting plate. The mounting plate is rotated and its planar surface is located with respect to the real time reference for each of the four sides of the mounting plate.

The image system scans for the real-time reference and locates the real-time reference by finding points of transition from white to black. Square apertures within the real-time reference are located. By knowing the size of the square apertures in the real-time reference, and the size of the pixels of the image, the relationship between pixels and mils can be computed.

Next, the image system scans for leads by examining the pixel intensity along vertical lines. The edges of a lead are located by finding white-to-black transitions. All leads are located for each of the four sides of the device, and then transformed with respect to the real-time reference.

The locations of all leads on all four sides of the device are determined with reference to the flat plate mounting surface which defines the x- and y-axes.

The lead end locations are computed for determining coplanarity using a three point plane or least squares fit.

The technical advance represented by the invention, as well as the objects thereof, will become apparent from the following description of a preferred embodiment of the invention, when considered in conjunction with the accompanying drawings, and the novel features set forth in the appended claims.

BRIEF DESCRIPTION OF THE DRAWINGS

FIG. 1 illustrates a folded optical path and the related components useable in the inspection system of the present invention;

FIG. 2 is a top view of part of the optical path;

DESCRIPTION OF A PREFERRED EMBODIMENT

Figure 3:
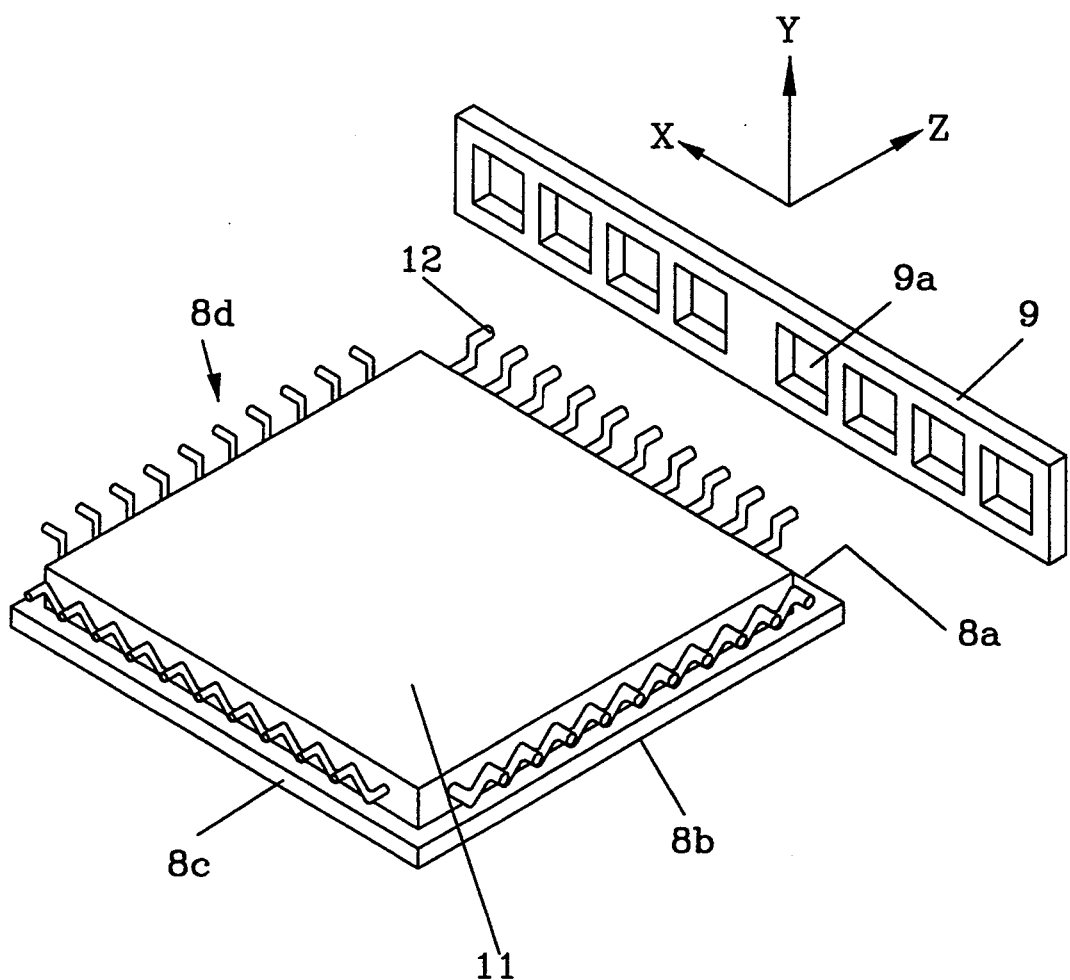
FIG. 3 shows the real-time reference, a mounting plate and a semiconductor device mounted thereon.

FIG. 1 shows the optical path and components for the component lead inspection system. A semiconductor device 11 having a plurality of leads 12 is mounted on a rotatable platform or base 8 in front of an illumination system 13. The illuminated device is viewed by camera 31 along path 14, through mirror assembly 17, is reflected back along path 15 to mirror 16 and reflected at a 45-degree angle along path 20 to mirror/beam splitter 21. The camera views the platform 8, the mounted semiconductor device 11 and a real-time reference 9.

When the image impinges on mirror/beam splitter 21, the image is reflected via path 24 to reflector 22, and back along path 25, through mirror/beam splitter 21, along path 28 to lens assembly 30, and then to camera 31.

The image passes through mirror/beam splitter 21 along path 26 to reflector 23, back along path 27 to mirror/beam splitter 21 and is reflected along path 29 to lens assembly 30 where it is focused on camera 31. It should be noted that during the splitting of the image at mirror/beam splitter 21, the two images may be separated vertically such that image 32 and image 33 are vertically and horizontally spaced and horizontally shifted from each other at camera 31.

Camera 31 is, for example, a full frame high resolution type camera such as the Kodak "MegaPlus" camera having improved reliability with the shutter removed. There is no need for an electro-mechanical shutter since the illumination source 13 is strobed at a rate to match that of the computer controlled image display system, presenting a continuous image of the device 11 and real-time reference 9.

FIG. 2 is a top view of the optical path represented by paths 14 and 15, and mirror assembly 17. Device 11 is in front of illumination source 13. An image of device 11 and the real-time reference is directed along path 14 to mirror assembly 17. Mirror assembly 17 includes two mirrors 18 and 19, oriented vertically and positioned at a 90-degree angle with respect to each other.

The image impinges on mirror 19, is reflected to mirror 18, and in turn is reflected along path 15 to mirror 16. Mirror 16 is positioned at a 45-degree angle from the horizontal plane, as illustrated in FIG. 1.

FIG. 3 shows the mounting platform plate 8, semiconductor device 11, and a real-time reference plate 9 with apertures 9a. In determining the planarity of leads 12 on each of the four sides of device 11, plate 8 has to be rotated to present each of the leads on the four sides of device 11. Plate 8 is rotatable and each of the four sides 8a, 8b, 8c and 8d are rotated toward the camera image path to place one of the device 11 sides toward the camera.

Figure 4:
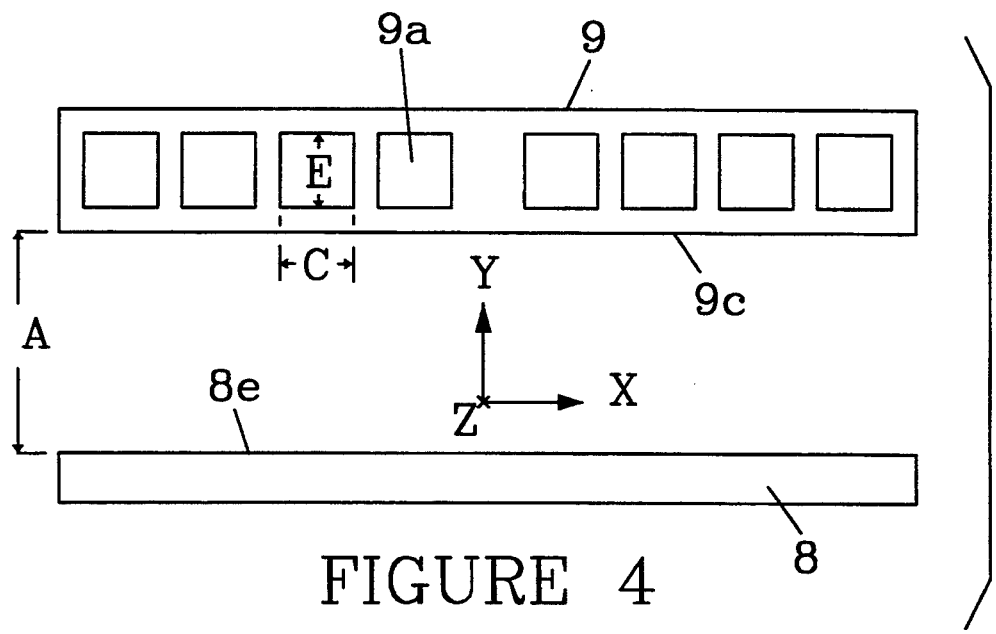
FIG. 4 shows the real-time reference and mounting plate as viewed from the image system.

FIG. 4 illustrates the mounting platform plate 8 and real-time reference 9 as viewed from the camera. In order to compensate for any slight variation of the distance from the top of plate 8 to the bottom of the real time reference, distance A is measured for each of the four sides of mounting plate 8. Each of the distances $A_1$, $A_2$, $A_3$ and $A_4$ is stored during a test to calibrate the image system using the real time reference 9. The distance A is measured for each of the four sides of plate 8, and the image system is calibrated to define the relationship between pixels and mils. The dimensions C and E of apertures 9a in real-time reference 9 are known; so, the number of pixels for the apertures can be related to linear measurement in mils. The position of top edge 8e of plate 8 is determined by the black-to-white transistions from the body of the plate to the space above the plate. The apertures 9a are also located and measured by white-to-black transitions from the aperture to the aperture frame.

Figure 5:
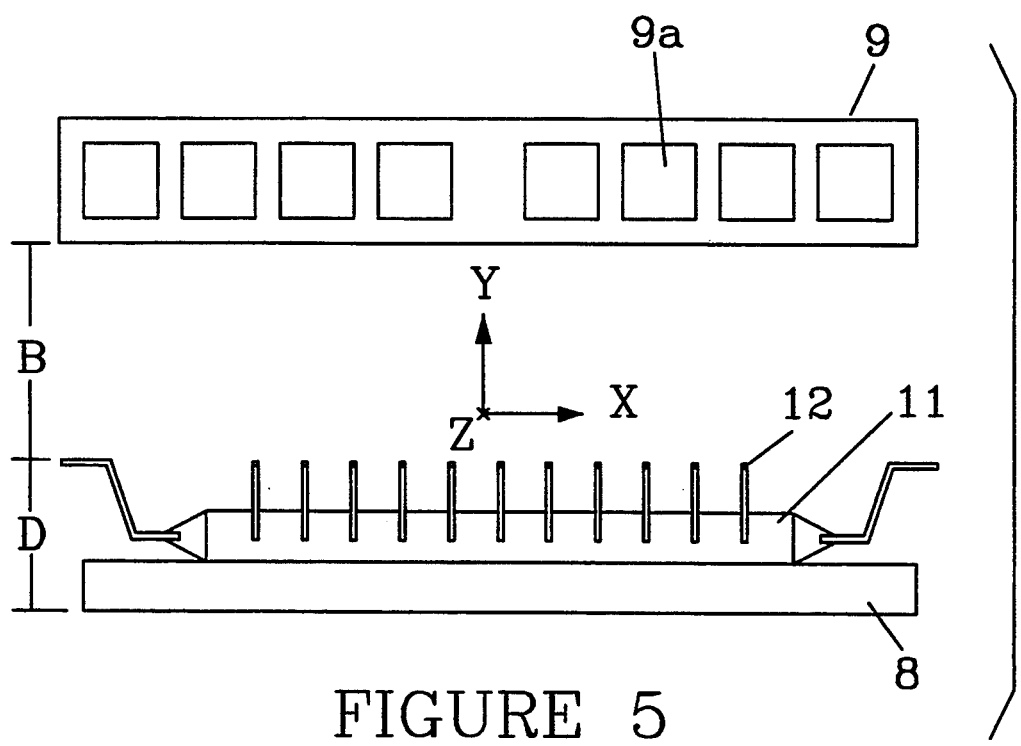
FIG. 5 shows the real-time reference, mounting plate and a semiconductor device.

FIG. 5 shows mounting platform plate 8 with a semiconductor device 11 mounted thereon. The distance B from the top of the lead 12 to the bottom of the real-time reference 9 is measured. Then the distance of the top of a lead 12 from the top of plate 8 can be calculated since the measurements $A_n - B_n = D_n$, where n is a number from 1 to 4, and represents the side of the semiconductor device for which the lead heights are being measured. $A_n$, as mentioned above, is measured for each side of plate 8, and only needs to be measured once during the inspection operation for a series of devices.

The system operation is as follows: The image system scans the real-time reference and locates the bottom edge straight line 9c by finding points of transition from white to black, black being the silhouetted image of the real-time reference. This location is with respect to the origin of a frame grabber within the image system. A number of bottom edge points are located along the real-time reference across the entire field of view, and a linear regression is computed through these points. This location procedure is also performed for each of the four sides 8a, 8b, 8c and 8d of mounting platform plate 8. Plate 8 is rotated for each of the measurements.

Next, the square apertures 9a within the real-time reference are located. By knowing the size of the square apertures 9a and the number of pixels across the aperture, a relationship between pixels and linear measure in mils is computed.

A semiconductor device is mounted on plate 8 and the image system scans for leads, and locates them with respect to the real-time reference. The system locates the edge of each lead by finding points of transition from white to black, where black is the lead image silhouetted against the light from illumination system 13. All leads are located. By knowing the relationship between pixels and mils, the exact location of each lead, for each of the four sides of the semiconductor device, is determined.

The locations of all the leads on all four sides of the semiconductor device are transformed with respect to plate 8, through the real-time reference, thereby determining the location of all the leads in three dimensions, with adjacent edges of plate 8 defining the x- and y-axes of the coordinate frame. The coplanarity of the leads is then computed using three-point plane or least squares fit calculations.

In testing semiconductors in an automated system, each device has the same orientation when it is placed on plate 8. Therefore, when data is reviewed for each device, any lack of coplanarity for any lead can be related to the exact side of the device.

Figure 6:
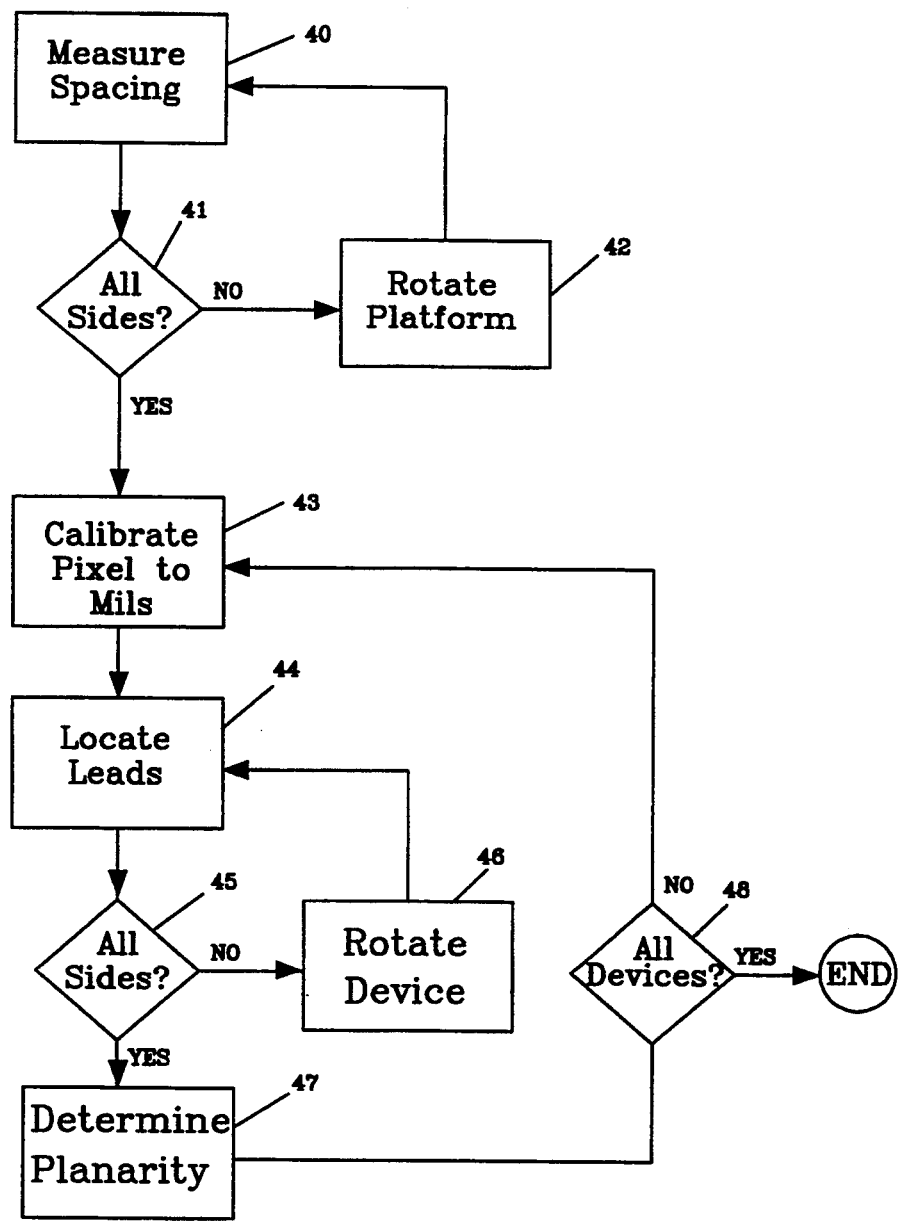
FIG. 6 is a block diagram showing the steps of the method for determining coplanarity.

FIG. 6 is a block diagram showing the basic steps in the method used in determining coplanarity. In Block 40, the distance A from the mounting plate 8 to the straight line bottom edge of real-time reference 9 is measured. Since the system must be calibrated for each of the four sides of plate 8, the measuring step is cycled through Block 41 and Block 42 until all four measurements have been made.

The next step is to calibrate the image correlating image pixels to linear measure, for example, in mils. This calibration is accomplished in Block 43 using the known x- and y-axes directional spacings C and E of edges of apertures 8.

The next step is to locate the leads based upon the calibration and location of the mounting platform plate 8 with reference to real-time reference 9. This procedure is cycled four times through Blocks 44, 45 and 46, to locate the leads on each of the four sides of the semiconductor device.

The last step, Block 47, is to determine the planarity of the leads in x-, and y- and z-axes coordinate space, based upon the foregoing four x- and y-spatial calibrations and measurements.

Block 48 determines if there are more devices to be tested and, if so, then the procedure loops back to Block 44 to test another device; if not, then the testing is ended.

The procedure loops back to Block 44 since the procedure in Blocks 40–43 has to be done only once for each testing period.

What is claimed:

1. A method, using an imaging system, for automatically measuring the coplanarity of lead ends of a surface-mounted semiconductor device; said device having at least two sides and a plurality of leads along each of said device sides; and said method comprising the steps of:

provniding a rotatable platform having a planar top surface and at least two sides; said platform sides respectively corresponding to said device at least two sides; and each platform side having a face with features respectively defining x- and y-axis directions;

providing a reference member fixed in spaced position relative to said platform; said member having a feature defining a straight line which is parallel to said plane of said platform top surface, and having at least a feature of known y-axis direction linear dimensional extent;

providing an imaging system, including a camera having a field of view simultaneously encompassing said rotatable platform and said reference member;

mounting said device on said top surface of said platform;

rotating said platform to successively present each side of said mounted device toward said camera so that, for each device side presented, said camera field of view simultaneously encompasses said presented device side, said platform side corresponding to said presented device side, and said reference member;

for each presented device side, grabbing an image of said camera field of view in pixel image form;

for each grabbed image, locating positions of said lead ends relative to positioning of said straight line;

from a pixel form image of said reference member known linear dimensional extent feature, identifying a scale factor relating pixels to linear dimensional measurement units; and using said position locations and said scale factor for the grabbed images, determining the coplanarity of said lead ends of said sides.

2. A method as defined in claim 1; wherein said reference member providing step comprises providing a reference frame fixed in spaced position above said platform top surface, said reference frame having a straight edge which is parallel to said platform top surface and which defines said straight line; and said locating step comprises locating positions of said lead ends relative to said straight edge.

3. A method as defined in claim 2, wherein said reference member providing step further comprises providing apertures in said frame; said apertures having aperture edges spaced apart by known distance in said y-axis direction; and said identifying step comprises identifying said scale factor based on pixel spacing of said aperture edges in said reference member pixel form image.

4. A method as defined in claim 3, wherein said reference member providing step further comprises providing said apertures having second aperture edges spaced apart by known distance in said x-axis direction; and wherein said locating step further comprises locating positions of leads of said mounted device relative to a common grabbed image reference point using said x-axis direction known spacing distance.

5. A method as defined in claim 4, wherein, in said reference member providing step, said apertures are squares with first and second sets of spaced apart opposite edges; said first set of edges being spaced apart by said known distance in said y-axis direction, and said second set of edges being spaced apart by said known distance in said x-axis direction.

6. A method as defined in claim 1, wherein, in said platform providing step, said platform is provided having fiat sides with adjacent edges respectively defining said x- and y-axis directions.

7. A method as defined in claim 1, wherein, in said locating step, said positions are located by finding points of transition between black and white in said grabbed pixel form images.

8. A method as defined in claim 1, further comprising the steps of, prior to mounting said device on said top surface:

rotating said platform to successively present each side of said platform toward said camera so that, for each platform side presented, said camera field of view simultaneously encompasses said presented platform side and said reference member;

for each presented platform side, grabbing an image of said camera field of view in pixel image form; and for each grabbed image, locating positions of a top surface edge relative to positioning of said straight line; and using said top surface edge position location to provide compensation for deviations from said parallel relationship of said straight line and said top surface in said coplanarity determining step.

9. A method, using an imaging system, for automatically measuring the coplanarity of lead ends of a surface-mounted semiconductor device; said device having four sides and a plurality of leads along each of said device sides; and said method comprising the steps of:

providing a rotatable platform having a planar top surface and four sides; said platform sides respectively corresponding to said device four sides; and each platform side having a fiat face with adjacent edges respectively defining x- and y-axis directions;

providing a reference frame fixed in spaced position above said platform top surface; said frame having a bottom edge defining a straight line which is parallel to said plane of said platform top surface, and having a plurality of apertures with first and second sets of opposite edges, respectively spaced apart in known x- and y-axis direction linear dimensional extents;

providing an imaging system, including a camera having a field of view simultaneously encompassing said rotatable platform and said reference frame;

mounting said device on said top surface of said platform, with said device sides generally aligned with said platform sides;

rotating said platform to successively present each side of said mounted device toward said camera so that, for each device side presented, said camera field of view simultaneously encompasses said presented device side, said platform side corresponding to said presented device side, and said bottom edge and plurality of apertures of said reference frame;

for each presented device side, grabbing an image of said camera field of view in pixel image form;

for each grabbed image, locating positions of said leads relative to positions of said straight line and said apertures;

from a pixel form image of said apertures, identifying a scale factor relating pixels to linear dimensional measurement units; and using said position locations and said scale factor for the grabbed images, determining coplanarity and displacements of said leads of said sides.

10. A method as defined in claim 9, further comprising the steps of, prior to mounting said device on said top surface;

rotating said platform to successively present each side of said platform toward said camera so that, for each platform side presented, said camera field of view simultaneously encompasses a top surface edge of said presented platform side, and said bottom edge of said reference member;

for each presented platform side, grabbing an image of said camera field of view in pixel image form; and for each grabbed image, locating positions of said top surface edge relative to said bottom edge; and using said top surface edge position location information to provide compensation for deviations from said parallel relationship of said straight line and said top surface in said coplanarity determining step.

11. A method as defined in claim 10, wherein, in each of said locating steps, said positions are located by finding points of transition between black and white in said grabbed pixel form images.

* * * * *